United States Patent [19]
Boyd et al.

[11] Patent Number: 5,491,734
[45] Date of Patent: Feb. 13, 1996

[54] OFF-AXIS SCANNING ELECTRON BEAM COMPUTED TOMOGRAPHY SYSTEM

[75] Inventors: Douglas P. Boyd, Hillsborough; Roy E. Rand, Palo Alto, both of Calif.

[73] Assignee: Imatron, Inc., South San Francisco, Calif.

[21] Appl. No.: 167,419

[22] Filed: Dec. 14, 1993

[51] Int. Cl.$^6$ ....................................................... H05G 1/60
[52] U.S. Cl. ................................................ 378/10; 378/4
[58] Field of Search ............................................ 378/10, 4

[56] References Cited

U.S. PATENT DOCUMENTS

| | | | |
|---|---|---|---|
| 5,172,401 | 12/1992 | Asari et al. | 378/10 |
| 5,193,105 | 3/1993 | Rand et al. | 378/137 |
| 5,197,088 | 3/1993 | Vincent et al. | 378/10 |

FOREIGN PATENT DOCUMENTS

| | | | |
|---|---|---|---|
| 6168032 | 6/1986 | Japan | 378/10 |
| 2044985 | 10/1980 | United Kingdom | 378/10 |

*Primary Examiner*—Craig E. Church
*Attorney, Agent, or Firm*—Flehr, Hohbach, Test, Albritton & Herbert

[57] ABSTRACT

A scanning electron beam CT system generates an electron beam along a beam source axis offset from the scanner axis, or axis of symmetry, thereby permitting the X-ray subject to pass completely through the stationary gantry. The electron beam is produced with the first drift tube region of an evacuated housing chamber, and is directed downstream toward a second region that includes a gantry. A scan target and a tuning target, each concentric with and defining a plane normal to the system axis of symmetry, are located in the gantry. A beam optics system, through which the electron beam passes, is located within the housing intermediate the electron gun and gantry. A control system focusses and scans the electron beam upon the scan target, maintaining a beam spot of desired quality. Upon impingement by the scanning beam spot, the scan target emits a fan beam of X-rays. A detector array, concentric with and defining a plane normal to the system axis of symmetry, is located opposite the scan target within the gantry and provides output signals that are computer processed to reconstruct a CT image of a subject placed within the gantry. The scanner axis is preferably above the beam source axis, and preferably the drift tube is straight, defining a drift tube axis that is inclined relative to the scanner axis, or is parallel to the scanner axis but not co-axial therewith. Alternatively, the drift tube may be kinked.

9 Claims, 8 Drawing Sheets

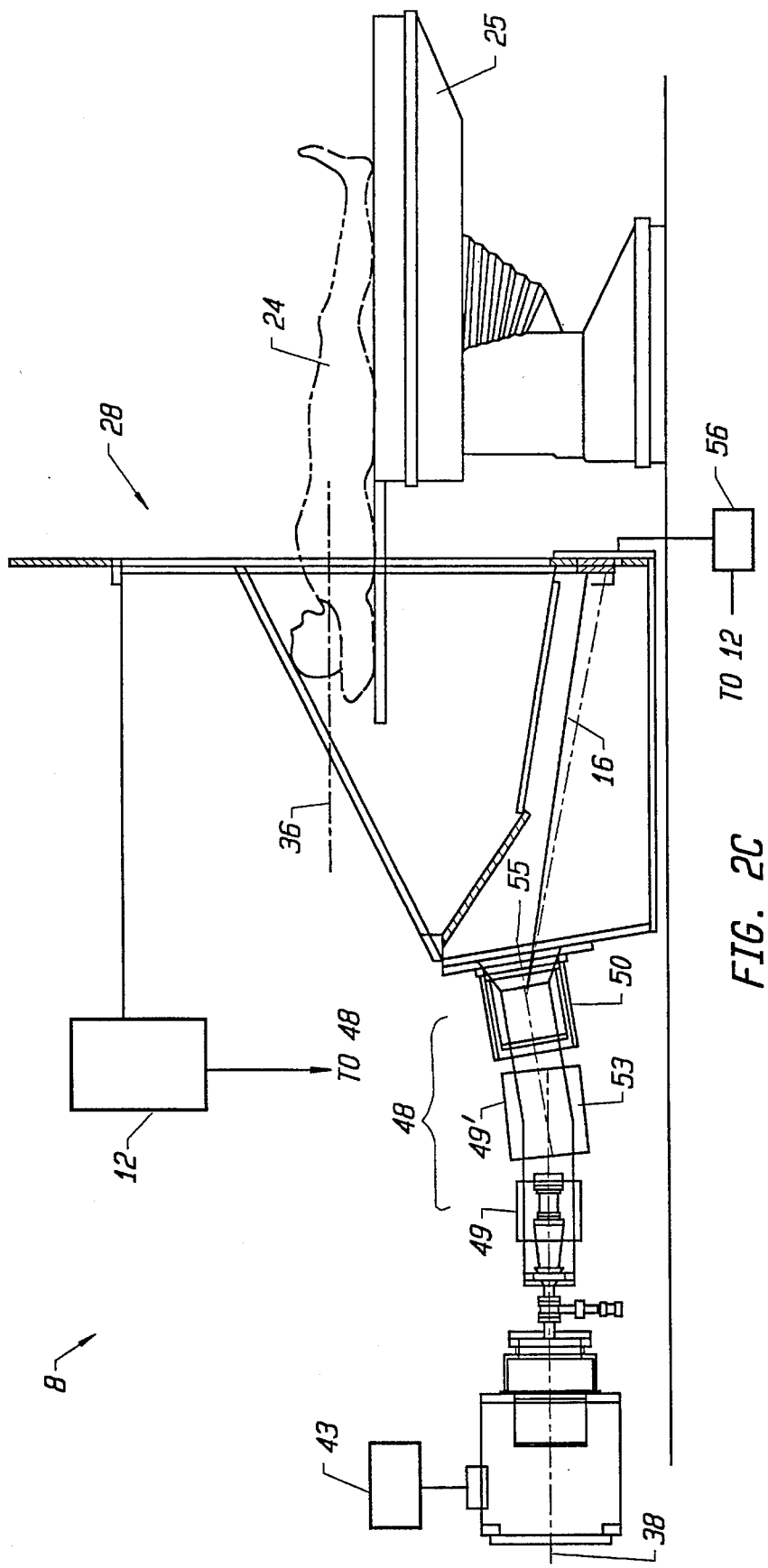

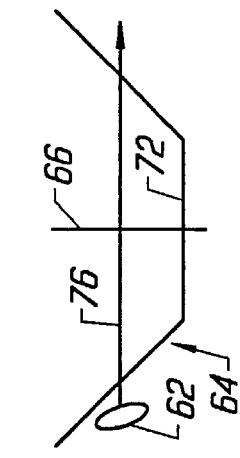
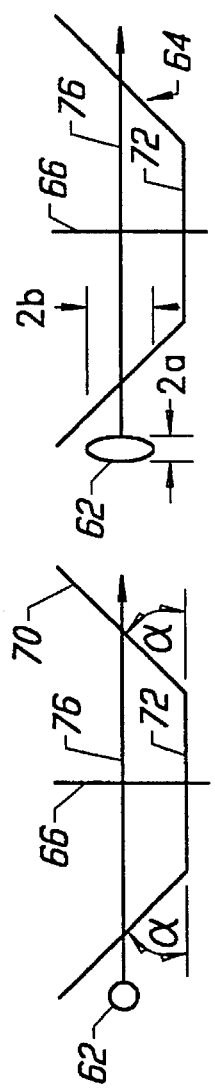
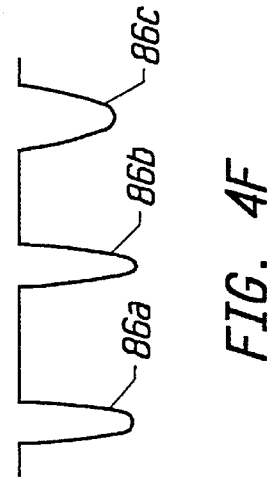
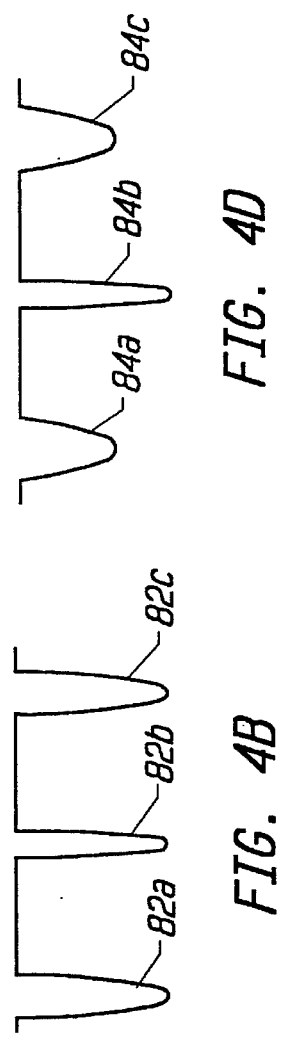

OFF-AXIS SCANNING ELECTRON BEAM COMPUTED TOMOGRAPHY SYSTEM

FIELD OF THE INVENTION

The present invention relates generally to scanning electron beam systems for X-ray production in a computed tomography X-ray transmission system, and more particularly to such a system wherein the electron beam source is offset relative to the scanner axis of symmetry.

BACKGROUND OF THE INVENTION

On-axis scanning electron beam computed tomography ("CT") systems are known in the art, and are described generally in U.S. Pat. No. 4,352,021 to Boyd, et al.), issued Sep. 28, 1982. The theory and implementation of devices to help control the electron beam in such systems is described in detail in several U.S. patents to Rand, et al., including U.S. Pat. Nos. 4,521,900 issued Jun. 4, 1985; 4,521,901 issued Jun. 4, 1985; 4,625,150 issued Nov. 25, 1986; 4,631,741 issued Dec. 23, 1986, and 5,193,105 issued Mar. 9, 1993. Applicants refer to and incorporate herein by reference each above listed patent.

As described in U.S. Pat. No. 4,521,900 to Rand, et al., in scanning electron beam CT systems, an electron beam is produced by an electron gun at the upstream end of an evacuated generally elongated and conical shaped housing chamber. A large electron gun potential (e.g., 130 kV) accelerates the electron beam downstream along a first straight line path. Further downstream, the beam optical system, which includes focus and deflection coils, deflects the beam into a scanning path.

The deflected and focussed beam exits the beam optical system and scans an arc-shaped target that produces X-rays when impinged by the beam. The X-rays penetrate an object (e.g., a person) and are detected by an arc-shaped array of detectors. The target and array of detectors are mounted in a stationary gantry, and are concentric about the scanner axis (or "axis of symmetry"), a precisely defined axis that is perpendicular to the planes of the target and detector array. The detected data are computer processed to produce a CT reconstructed image of a portion (or slice) of the object.

Briefly, in the upstream chamber region between the electron gun and the focus and deflection coils a diverging electron beam is desired, but in the region downstream from the focus and deflection coils, a converging electron beam is desired.

In the upstream region, the electrons' space-charge advantageously causes the electron beam to diverge or expand. Expansion here is beneficial because the beam width at the target varies approximately inversely with the beam diameter at the focus and deflection coils. Unless removed from this region, positive ions can neutralize the space charge and prevent beam divergence, destabilizing or even collapsing the beam. Positive ions, which are produced from the interaction of the electron beam with gases remaining in the chamber after evacuation, are undesired in the upstream chamber region. An ion clearing electrode ("ICE"), coupled to perhaps a 1 kV potential, is mounted in the upstream chamber region to remove positive ions. The electron beam passes axially through the ICE, which creates a relatively large transverse electric field that sweeps away the slow moving positive ions, without disturbing the considerably faster moving electrons.

In the downstream region, positive ion neutralization is beneficial, since a converging, self-focussing, electron beam is desired. Elements in the beam optical system then fine tune the converged beam to produce a small electron beam spot and consequently a sharp X-ray image.

In summary, ideally, the electron gun and beam optics system are perfectly cylindrically symmetric, producing a perfectly homogenous electron beam having uniform electron distribution. Such an ideal beam would act as its own perfect lens: self-diverging in the upstream chamber region and self-converging in the downstream chamber region, to focus sharply on the target. In practice, if the electron gun is not ideal, beam uniformity should be corrected by the beam optical system.

In the prior art, the source of the electron beam (e.g., the electron gun, drift tube and beam optics) was coaxial with the scanner axis, forming an "on-axis" system. The configuration advantageously provided a substantially constant distance between the electron beam optic system and the arc-shaped target, facilitating maintenance of a sharply focused, elliptical shaped beam spot at all points along the scanned target.

Unfortunately, the on-axis configuration prevented the X-ray subject from passing completely through the gantry because the electron gun end of the conical chamber would be struck by the subject couch. By contrast, mechanical CT X-ray systems such as described in U.S., Pat. No. 4,630,202 to Mori permit the subject to move completely through a rotating gantry, but cannot provide sub-second single scans that eliminate motion artifacts, including heart motion, as can scanning electron beam CT systems.

What is needed is a scanning electron beam CT system that is off-axis, to allow an X-ray subject to pass completely through the gantry.

The present invention discloses such a system.

SUMMARY OF THE INVENTION

The present invention provides a scanning electron beam CT system whose electron beam is generated along a beam source axis that is offset from the scanner axis, or axis of symmetry. The off-axis configuration permits the X-ray subject to pass completely through the stationary gantry.

The system includes an evacuated housing chamber having a first, drift tube, region wherein an electron beam is produced and directed downstream toward a second region that includes a gantry. An arc-like scan target and a tuning target are located in the gantry. The scan and tuning targets are each concentric with and define a plane normal to the system axis of symmetry. A beam optics system, located within the housing intermediate to the electron gun and gantry, includes at least one dipole coil, a solenoid coil, and quadrupole coils, as well as an ion-controlling electrode assembly through which the electron beam passes. A control system focusses and scans the electron beam upon the scan target, maintaining a beam spot of desired quality. Upon impingement by the scanning beam spot, the scan target emits a fan beam of X-rays. A detector array that is concentric with and defines a plane normal to the system axis of symmetry is located opposite the target within the gantry.

An object to be examined is positioned within the gantry between the target and the detector array such that some X-rays will be attenuated by the object. The detector array provides output signals proportional to the intensity of the detected X-rays. A signal processing system converts the output signals to form a reconstructed CT image of a slice of the object under examination.

The scanner axis is offset, preferably higher, relative to the source of the electron beam, namely the electron gun, the drift tube and beam optics system. This configuration permits an object to pass axially completely through the gantry, over the first housing region. The drift tube may be straight, and may define a drift tube axis that is tilted relative to the scanner axis. Alternatively, the drift tube may be straight and parallel to the scanner axis but not co-axial therewith, or the drift tube may be kinked.

Other features and advantages of the invention will appear from the following description in which the preferred embodiments have been set forth in detail in conjunction with the accompanying drawings.

BRIEF DESCRIPTION OF THE DRAWINGS

FIG. 2C depicts a third embodiment of an off-axis scanning electron beam CT system, according to the present invention;

FIGS. 4A–4F depict electrical signals provided by the beam spot intercepting devices as a function of beam spot shape, according to the present invention.

DETAILED DESCRIPTION OF THE PREFERRED EMBODIMENTS

Figure 1:
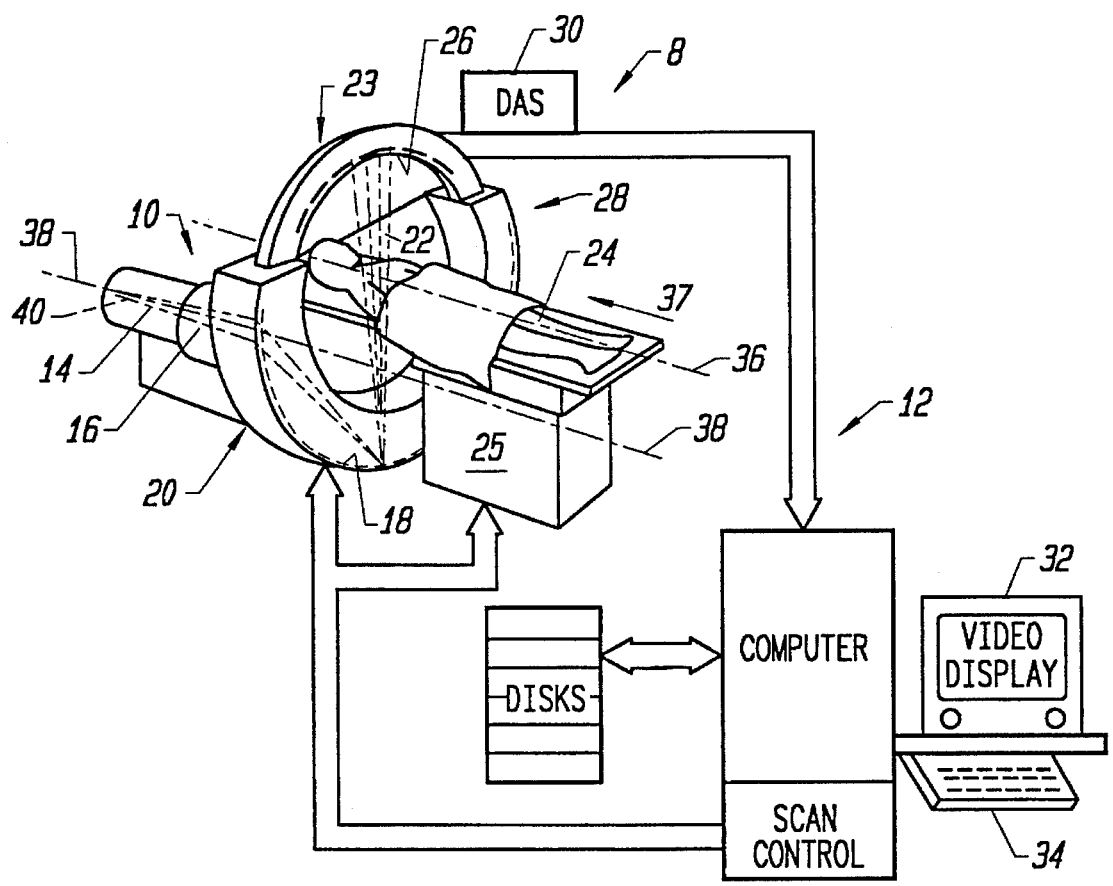
FIG. 1 depicts a generalized off-axis scanning electron beam CT system, according to the present invention.

FIG. 1 and FIG. 2 depict a generalized off-axis computed tomography X-ray transmission scanning system 8 according to the present invention. System 8 preferably includes a scanner 10, and an associated computer control system 12. Scanner 10 includes a vacuum housing chamber 14 wherein an electron beam 16 is generated and caused to scan an arc-shaped target 18 located within and extended around the inside of chamber 14's front lower portion 20. Typically, chamber 14 has a dimension L ranging from about 2 m to 3 m, although other dimensions could also be used.

Upon being struck by the electron beam, which typically scans 210° or so in about 50 ms, the target emits a moving fan-like beam of X-rays 22 that pass through a region of a subject 24 (e.g., a patient or other object), lying atop a couch moving mechanism 25, and then register upon a detector array 26 located diametrically opposite. The ring-like assembly housing target 18 and detector array 26 will be referred to collectively as gantry 28. Target 18 and detector array 26 are concentric about the scanner axis 36, and define planes normal to that axis.

The detector array outputs data to a data acquisition system ("DAS") 30 that digitizes and passes the data to the computer system 12. Computer system 12 further processes and records the data to produce a reconstructed image of a slice of the subject 24 on a video monitor 32. An X-ray technician via keyboard 34 can operate computer system 12 to control the overall operation of system 8, including the production and control of the electron beam 16 and movement of patient 24. It is understood that system 8 may be operated in a conventional mode and/or in a helical mode.

In a significant departure from on-axis prior art systems, the scanner axis 36 is offset relative to the axis 38 of the source of the electron beam 16. In FIG. 1, the scanner axis 36 is about 1 m above and parallel to floor 39, and preferably is higher than the beam axis 38 by 60 cm to 80 cm, although other dimensions could instead be used. Because there is an offset, subject 24 can pass completely through gantry 28 without striking chamber 14.

The generation of the scanning electron beam 16 will now be described with reference to FIG. 2A. An electron gun 40 within the upstream end 42 of chamber 14 produces the electron beam 16 in response to high voltage excitation (e.g., 130 kV) from power supply 43. Although a vacuum pump (not shown) evacuates chamber 14, gases remain that can produce positive ions in the presence of the electron beam 16.

An electrode assembly 46 is disposed within the chamber 14, between the electron gun 40 and beam optical system 48, coaxially along the optic or beam system axis 38, such that electron beam 16 passes axially therethrough.

The electrode assembly 46 typically includes one or more ion clearing electrodes ("ICE's"), and an optional periodic axial field ion controlling electrode ("PICE"), located at the most upstream region of the electrode assembly and, downstream therefrom, a positive ion electrode ("PIE"). However, if the electron gun 40 is sufficiently imperfect, electrode assembly 46 may also require a rotatable field ion controlling electrode ("RICE").

ICE units are known in the art, and are disclosed in U.S. Pat. Nos. 4,625,150 and 5,193,105 to Rand, et al. Briefly, an ICE is a unit mounted coaxially about the electron beam that includes at least two diametrically opposing constant radius element pairs forming a cylinder. Typically, a large negative potential (e.g., −1.5 kV) is coupled to one element, 0 V to its opposing element, and an intermediate voltage (e.g., −750 V) is coupled to the opposing remaining elements. These potentials cause the ICE to sweep away all positive ions in any region of the housing chamber between the electron gun and beam optics that is not otherwise controlled, e.g., by a RICE, PIE or a PICE (if present).

U.S. Pat. No. 5,193,105 also describes a short-length periodic axial field ion controlling electrode ("PICE"), disposed adjacent the electron gun in the upstream region of the housing chamber where small size and discontinuities may preclude the effective use of a conventional ICE. The PICE comprises several spaced-apart washer-like electrodes coaxial to the optic axis, with alternate electrodes coupled to a relatively large potential (e.g., −2 kV) relative to intermediate electrodes (e.g., 0 V). The PICE's small size allows it to operate in the upstream housing chamber region across discontinuities and thus remove positive ions from this region.

If electron gun 40 is sufficiently imperfect, electrode assembly 46 may require a RICE to homogenize the electron beam space-charge density by controlling any positive ions allowed to remain within the RICE. As disclosed in U.S. Pat.

No. 5,193,105, a RICE includes at least two pairs of spaced-apart elements, an equal and opposite electrical potential preferably being coupled to each element in an element pair. The elements comprising each element pair are preferably cylindrically symmetrical to each other about the beam axis. The RICE structure expands downstream such that the distance from the beam axis to each RICE element is approximately proportional to the electron beam radius at each point. This geometry tends to make the potential along the beam axis constant so ions trapped within the electron beam will not tend to drift axially and produce severe beam optical aberrations.

As further described in U.S. Pat. No. 5,193,105, electrode assembly 44 may include a positive ion electrode ("PIE"). The PIE is disposed coaxially downstream from the ICE or RICE, and is biased to create a large axial field preventing upstream migration of positive ions that could interfere with the production of a sharply self-focused uniform beam at the X-ray target.

Because the theory and use of components comprising electrode assembly 44 are thus known in the art, further details are not here presented.

Optical system 48 is disposed downstream from electrode assembly 44, and comprises a focus solenoid coil 49, and a combination of dipole coils/quadrupole coils 50. The focus solenoid and quadrupole coils magnetically focus and fine tune the electron beam convergence, scanning beam 12 across target 18. A tuning target 19 and W-wires 21 enable beam mechanism 56 and computer system 12 to monitor the actual shape and position of the electron beam spot upon target 18 at all scan points. Although magnetic deflection is preferably used, other deflection systems could instead be used, e.g., an electric field focussing system.

Figure 2A:
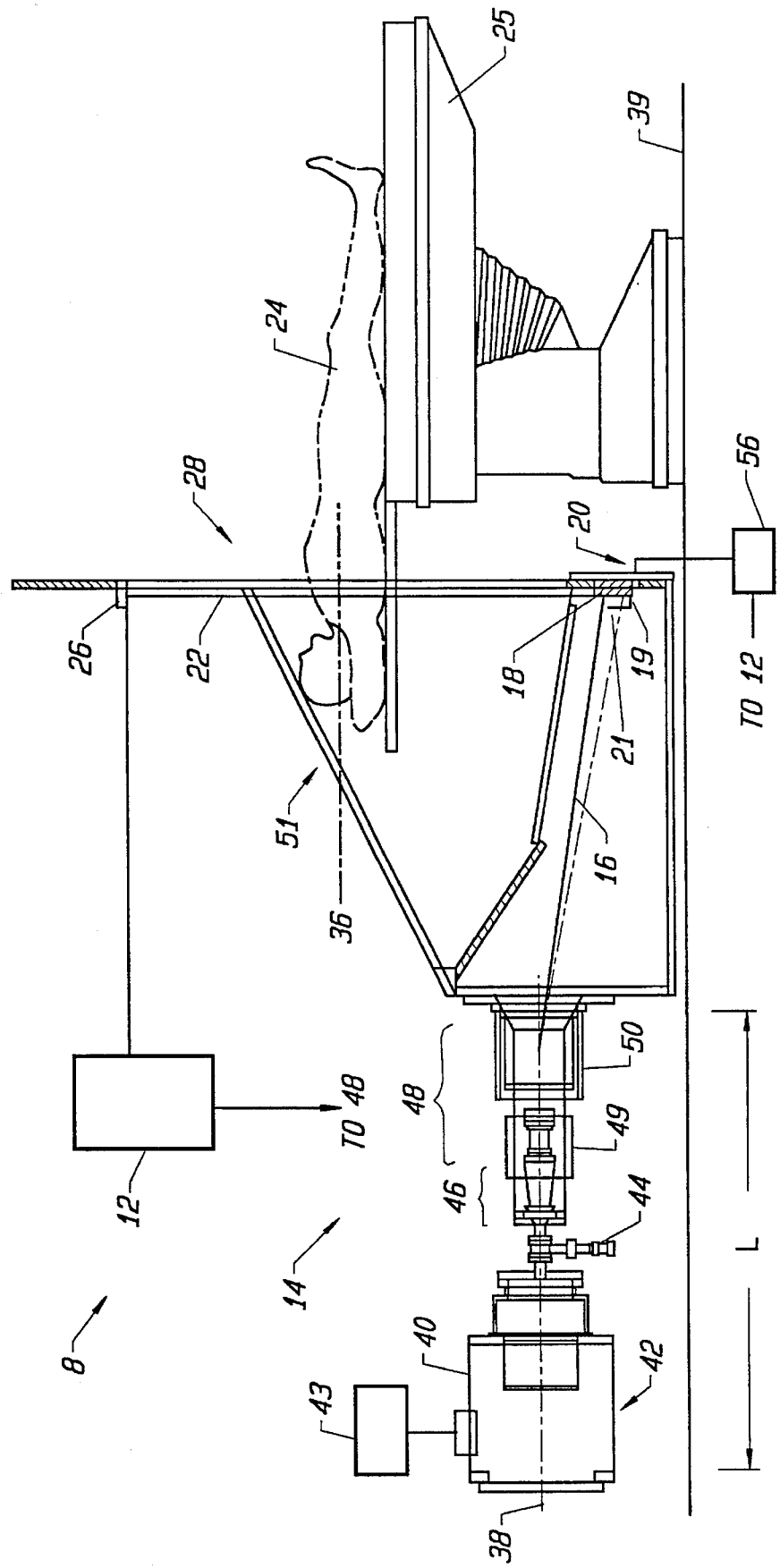
FIG. 2A depicts a first embodiment of an off-axis scanning electron beam CT system, according to the present invention.

The off-axis configuration of FIG. 2A has several drawbacks, including the aperture of the dipole 49 possibly limiting the angle of deflection of electron beam 16. To compensate for this, the offset cone 51 (or vacuum chamber) must be lengthened to permit the electron beam to traverse the uppermost portion of target 18, typically 30 cm above scanner axis 36. This limitation may be overcome, however, by tilting the dipole, as in the embodiments of FIGS. 2B, 2C, 2D and 2E.

Figure 2B:
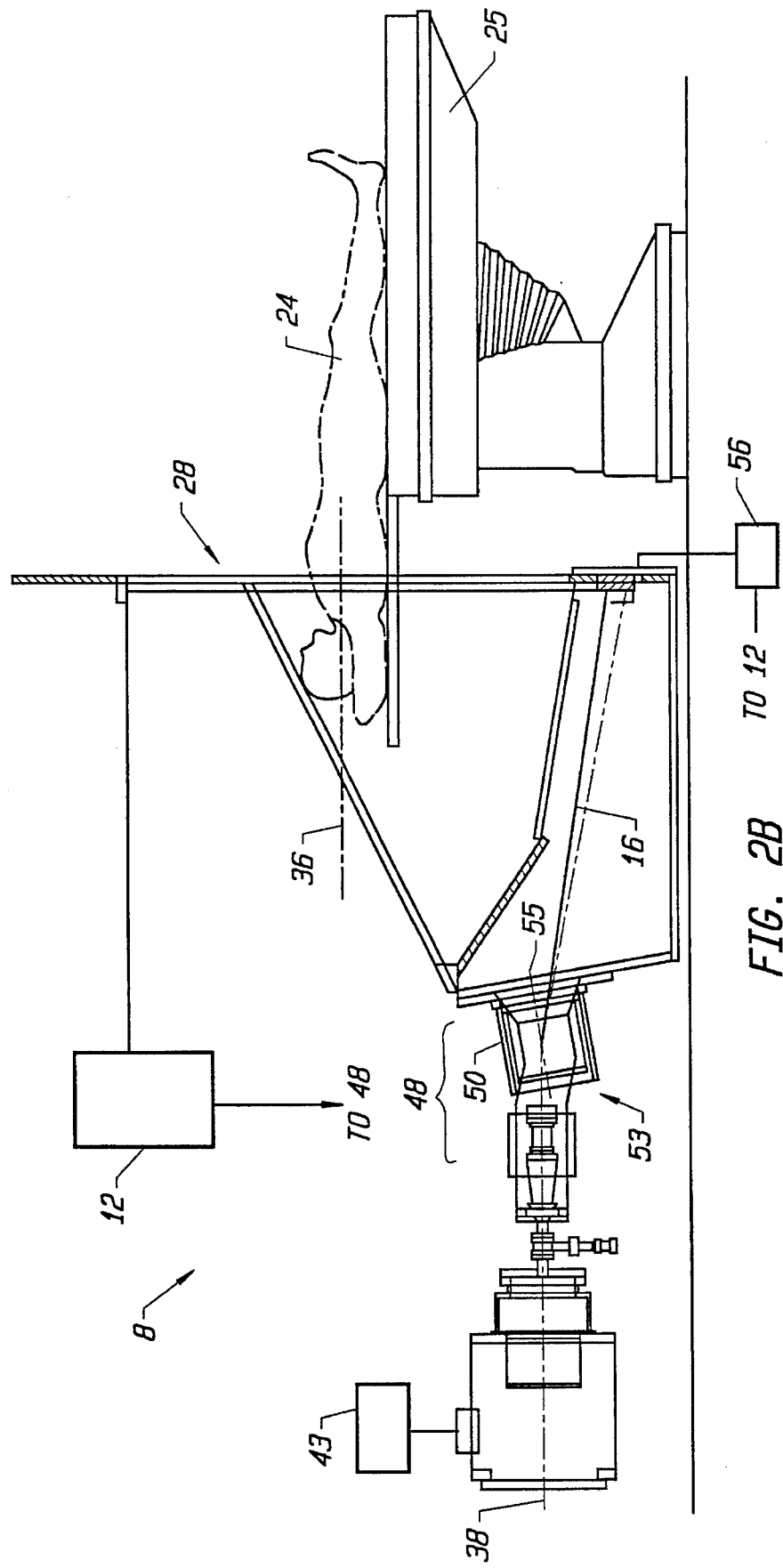
FIG. 2B depicts a second embodiment of an off-axis scanning electron beam CT system, according to the present invention.

FIG. 2B shows an embodiment of system 8 wherein dipole 50 is tilted relative to the beam optic axis 38 by about 0° to about 20°. To accommodate this tilt, the drift tube must be kinked at region 53. While this configuration overcomes the transverse aperture limitation described above, beam 16 no longer enters dipole 50 coaxially with the dipole axis 55, and beam optical aberrations may result.

Figure 2D:
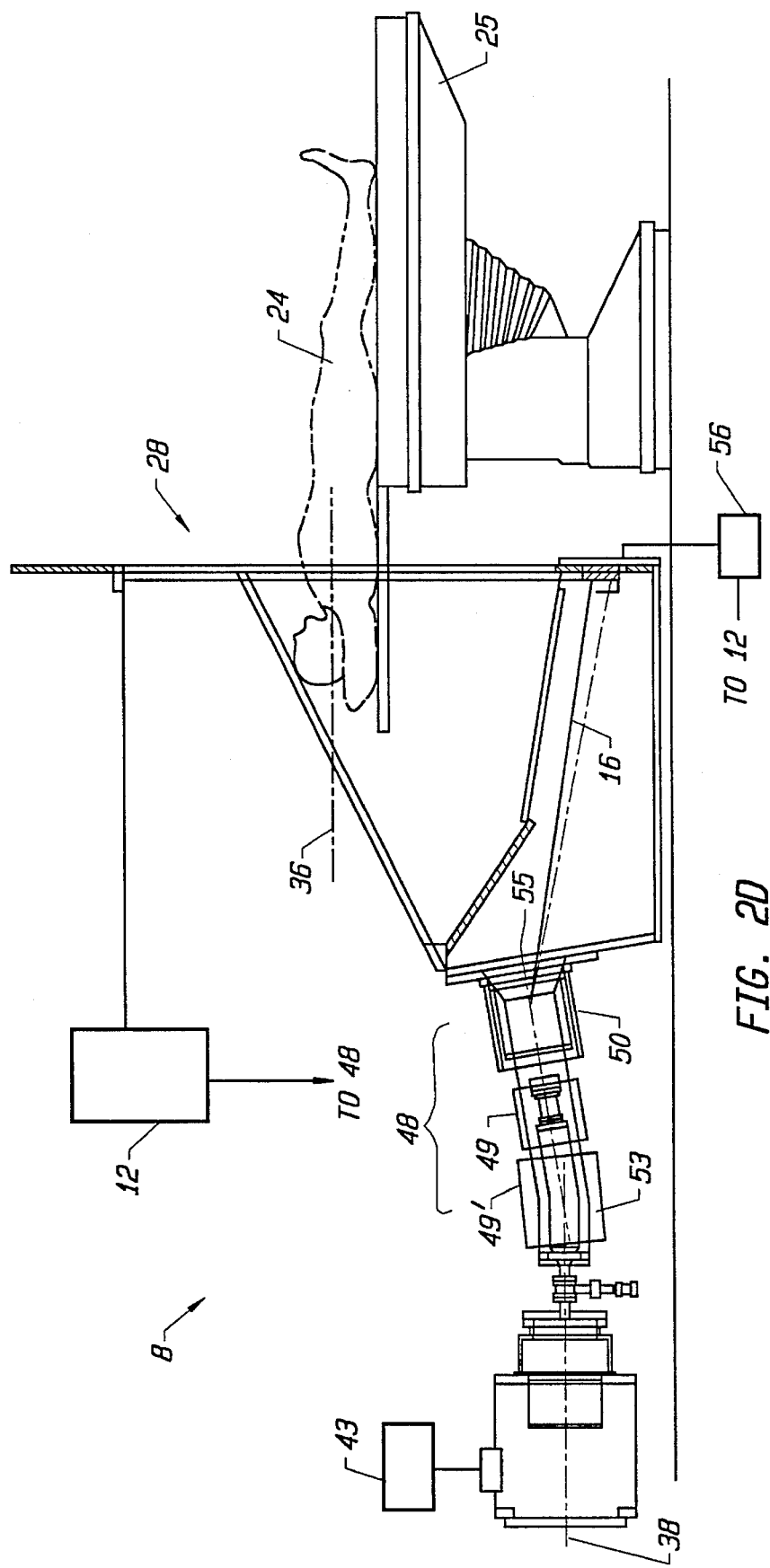
FIG. 2D depicts a fourth embodiment of an off-axis scanning electron beam CT system, according to the present invention.

FIGS. 2C and 2D show embodiments of system 8, that includes a second dipole (or deflection magnet) 49' that forces beam 16 to enter the dipole on-axis, thereby reducing beam optical aberrations. Preferably the tilt angle is between about 0° and about 20°. In FIG. 2C, dipole 49' is located downstream of solenoid 49, and in FIG. 2D, dipole 49' is located upstream of solenoid 49. In either configuration, the drift tube contains a kinked region 53. While the cone region is shorter, the drift tube length increases to accommodate the second dipole 49'.

Figure 2E:
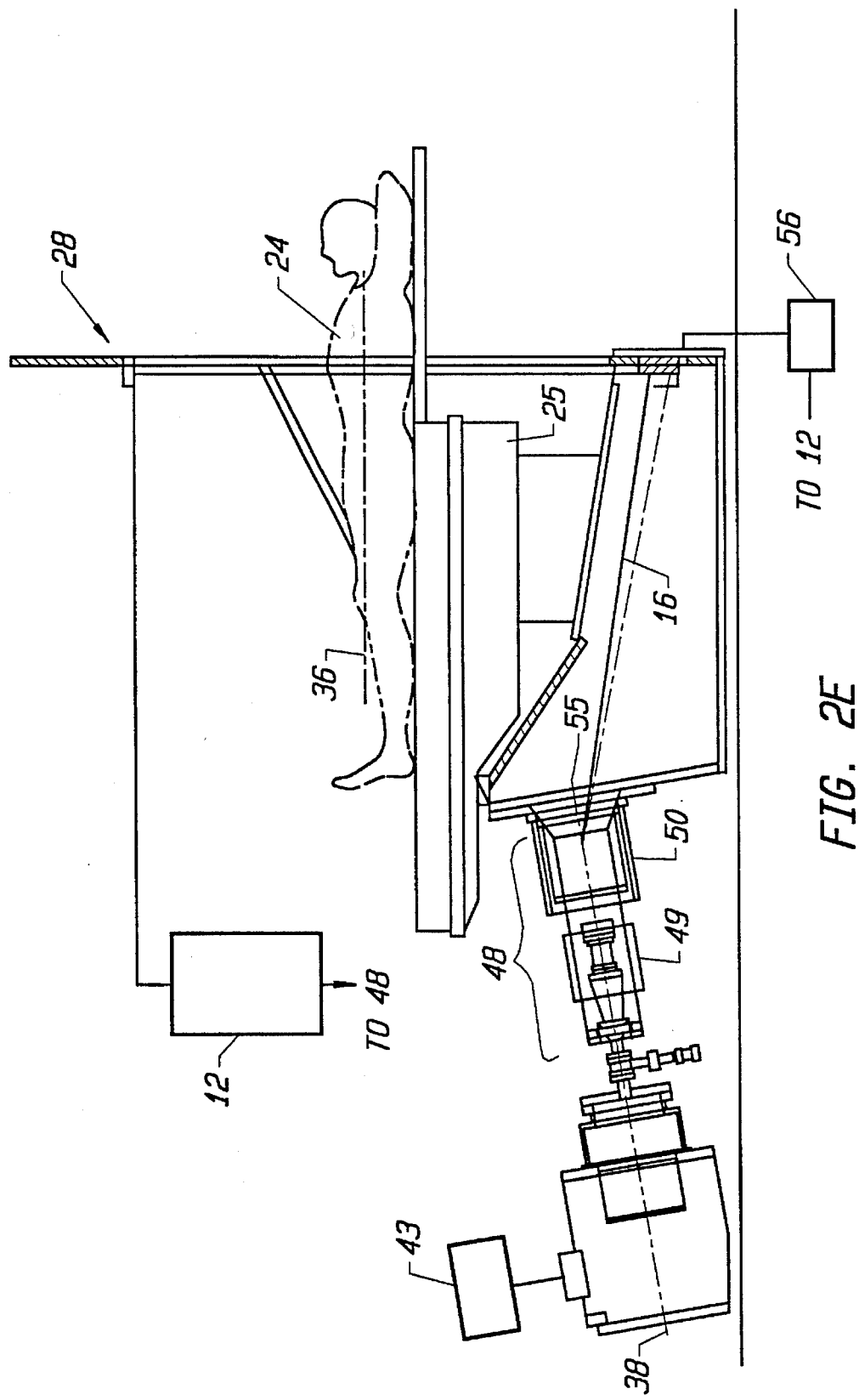
FIG. 2E depicts a fifth embodiment of an off-axis scanning electron beam CT system, according to the present invention.

FIG. 2E shows an embodiment wherein the drift tube is straight, but inclined relative to scanner axis 36, by about 0° to about 20°. FIG. 2E also demonstrates that an off-axis configuration according to the present invention permits the patient table or couch 25 to be mounted in a "downstream" or an "upstream" configuration. The latter configuration, depicted in FIG. 2E, can advantageously reduce the space required to install the scanner system and may also provide clinical advantages. It is to be understood that each of the off-axis configurations depicted in FIGS. 2A–2D can also accommodate mounting the patient couch in an "upstream" orientation.

The beam mechanism 56 and associated components will now be described. With reference to any of FIGS. 2A–2E and to FIG. 3, the electron beam 16 is caused by beam optical system 48 to scan along the arc-like X-ray target 18 along an operating scan path 80. Computer system 12 may also cause the dipole coils to move the beam spot along a monitoring scan path 76.

As explained in U.S. Pat. No. 4,521,901, preferably the electron beam should form a beam spot upon target 18 that is elliptical in shape. Adjustment of the beam optics is complicated in the present invention because an off-axis configuration causes the distance from the beam optics assembly 48 to target 18 to vary.

For example, in FIG. 2A, it is farther from assembly 48 to a scan point on target 18 higher than patient 24's head than to a scan point on target 18 at the same height as optic axis 38. Also, the plane of the beam deflection differs from the plane containing the major axis of the desired elliptical beam spot upon target 18.

Monitoring arrangements for maintaining a desired elliptical beam spot at all scan points on target 18 in an on-axis CT system are disclosed in U.S. Pat. No. 4,631,741 to Rand, et al., and in U.S. Pat. No. 5,224,137 to Plomgren, et al. These beam spot monitoring arrangements are preferred in the present invention, although other monitoring methods are also possible.

Figure 3:
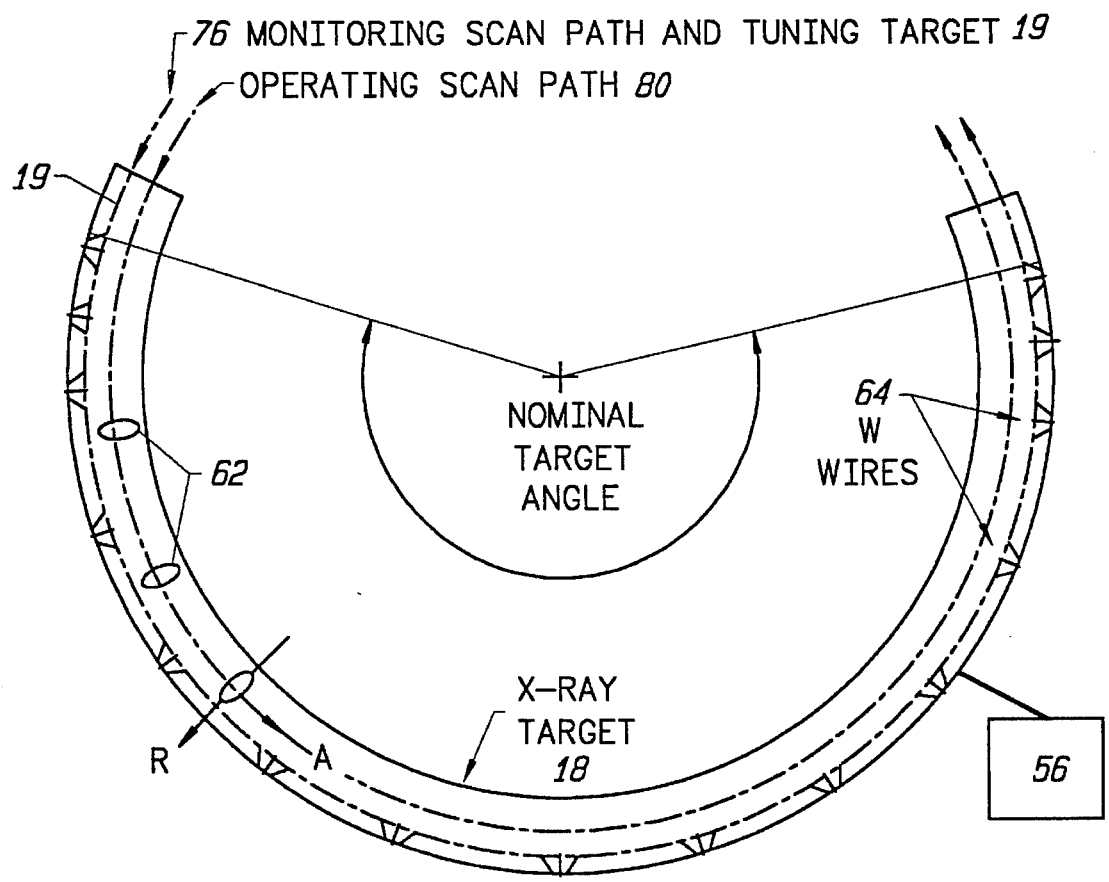
FIG. 3 depicts the relationship between the scanning target and the tuning target, and beam spot intercepting devices, according to the present invention.

With reference to FIG. 3, as electron beam 16 impinges upon target 18 along operating scan path 80, it forms a beam spot 62 that is preferably elliptical in shape. This elliptical beam spot 62 has a major axis normal to the scan path and extending in the radial direction indicated by R, and a minor axis extending in the azimuth direction indicated by A. This preferably elliptical beam spot 62 is created by the solenoid coil, quadrupole coils, and dipole coils within beam optical system 48, which use differential focal strength optics to focus the electron beam to a spot on the target. This preferred focusing mechanism maintains the desired elliptical shaped beam spot at all points along the scan path.

With reference to FIGS. 2A–2E, the present invention includes mechanism 56 for monitoring the actual shape and position of the electron beam spot 62 upon the tuning target 19, which is outside X-ray target 18, as shown in FIG. 3. Associated with tuning target 19 are a plurality of "W"-shape electron beam intercepting devices 64. Devices 64 produce an electrical signal upon impingement by the electron beam 16 as it scans across the tuning target 19 such that the signal configuration varies with the position and shape of the electron beam spot 62. Devices 64 are preferably located away from the operating scan path 80, and outside the range of X-ray collimators used in the system, such that if stray electrons strike devices 64, the resultant X-rays cannot reach the scanner detectors 26 (see FIG. 1).

In conjunction with computer system 12, mechanism 56 monitors the quality of the electron beam and may make suitable corrections to maintain proper beam spot quality along tuning target 19.

Beam intercepting devices 64 preferably take the form of a generally W-shaped electrically conductive wire, preferably made of tungsten. Devices 64 have a component 66 that extends orthogonally across monitoring path 76 (see FIG. 3), components 68, 70 that extend across path 76 at an angle α, and a component 72 that clamps wires 68, 70 together. A suitable conductive lead (not shown) electrically couples device 64 to mechanism 56 and thus to an oscilloscope or to computer system 12 (see FIG. 1).

As shown by FIGS. 4A–4F, the electrical signals produced by the intercepting devices 64 upon impingement vary with the position and shape of the beam spot 62 at that particular device. Consider first a circular beam spot that is perfectly aligned radially, indicated as 62' in FIG. 4A. As shown in the oscilloscope depiction of FIG. 4B, the resulting electrical signal produced as the electron beam scans past device 64 consists of three equal height pulses 82a, 82b, and 82c. However, because the outer components of device 64 extend across monitoring path 76 at an angle α, the outside pulses 82a and 82c are wider than the central pulse 82b.

Assuming that the scan speed of the beam spot is constant, the spatial relationship between the pulses 82 will vary with the radial (lateral) position of the beam spot 62 on path 76, e.g., with the vertical position of the beam spot as it is viewed in FIG. 4A.

If the beam spot crosses device 64 at points further away from the base segment 72, the time between pulses will increase, and if the beam spot is closer to base segment 72, the time between pulses will decrease.

The above-described time information is used to adjust the electron beam to place the beam spot in the center of its scan path. Unequal spacings between the pulses 82 would indicate that the actual scan path taken by the beam spot has a radial component, which can be corrected. Moreover, the time of arrival of the beam spot at the device 64, e.g., the azimuthal or longitudinal position of the beam spot, can be measured by comparing each device 64's pulses 82 with a timing pulse generated by computer system 12, which controls the operation of the overall system 8. Beam spot means 56 and computer system 12 can provide a mechanism that generates such timing pulses. If such timing pulses and pulses 82 are in sync with one another in a predetermined way, the beam spot will be at the desired longitudinal position (e.g., in the right place at the right time). Thus, by observing these two pulse types, the longitudinal position of the beam spot can be monitored.

The foregoing discussion described how a circular beam spot 62' interacts with an electron beam intercepting device 64. While the present invention is compatible with a scanning electron beam having a circular beam spot, the preferred embodiment provides an elliptical beam spot, as discussed previously. Such preferred elliptical beam spot will have its major axis in the scanner's radial direction, (e.g., perpendicular to the scan path), and its minor axis in the azimuthal direction. The interaction between an ideal elliptical beam spot 62 and a device 64 is depicted in FIGS. 4C, with corresponding output pulses 84a, 84b, and 84c depicted in FIG. 4D.

For the example of FIGS. 4C and 4D, it is assumed that the beam spot is properly oriented so that its major axis is normal to the scan path and the beam spot is centrally located on the scan path. Further, the minor axis is assumed to be equal to 2a while the major axis is assumed to be equal to 2b, as illustrated in FIG. 4C. The width of the inner pulse 84b is a measure of 2a, and the width of the outer pulses 84a, 84c is a measure of 2b. As in the case of the circular beam spot, if the elliptical beam spot 62 varies laterally (radially) within the scan path, the pulses 84 will move closer together or further apart.

FIGS. 4E and 4F show how the beam intercepting device 64 interacts with beam spot 62 when the latter is incorrectly oriented, that is, skewed counterclockwise as shown. As shown in FIG. 4F, the first two pulses 86a, 86b mimic the pulses 82a, 82b (corresponding to the circular beam spot 62' in FIG. 4B), while the third pulse (86c) is smaller in amplitude and wider. Had the beam spot been skewed in the opposite direction, pulse 86a would be shorter and wider.

In this fashion, devices 64 are used to monitor the profile and lateral position of the beam spot and beam orientation (assuming a non-circular beam spot) by producing pulses corresponding to those shown in FIGS. 4B, 4D and 4F. Further, by determining beam spot arrival time at the various devices 64, such pulses can be used to correct for errors in the beam spot profile, orientation and position (laterally and longitudinally) on monitoring scan path 76.

After the beam spot is focused, aligned and properly positioned on monitoring scan path 76 at each device 64, its path radius is decreased by a known amount at each device to define the previously recited operating scan path 80.

Beam tuning or adjustment may be achieved by a manual system that allows the operator to adjust the coil current for the various devices comprising the beam optical system (e.g., dipoles, quadrupoles, and solenoid) at the times when the beam spot is at the W-wire locations. There are five beam spot attributes that may be specified: time, radial position, spot length, spot width and spot orientation. Since there are five beam optical system coil currents that may be adjusted (e.g., two dipole coils, two quadrupole coils, one solenoid coil), there will always be a set of coil currents that achieve the desired beam spot specifications.

Tuning is performed by observing the signal from a particular W-wire on an oscilloscope while adjusting the beam optics system coil currents at the corresponding time so that the shape of the signal complies with the specifications. A properly tuned signal is similar to the pulse shape down in FIG. 4D. When the coil currents at the W-wire points are thus established, the values at intermediate times may be found by interpolation. In principal, this tuning process may be automated in a manner similar to that described by U.S. Pat. No. 5,224,137 to Plomgren, et al., to improve precision and speed.

Modifications and variations may be made to the disclosed embodiments without departing from the subject and spirit of the invention as defined by the following claims.

What is claimed is:

1. An off-axis scanning electron beam computed tomography scanner system having a scanner axis of symmetry, comprising:

an evacuated housing chamber having a first, drift tube, region wherein an electron beam is produced and directed downstream toward a second region that includes a gantry;

an X-ray producing scan target, disposed within said gantry, that emits a fan beam of X-rays upon impingement by said electron beam, said electron beam being substantially perpendicular to a plane defined by said scan target, and said scan target being concentric with and defining a plane normal to said axis of symmetry;

means, disposed intermediate said first and second regions, for focusing and directing said electron beam upon said scan target in a chosen scan path, said electron beam defining a beam spot along said scan path; and detector means for measuring intensity of said fan beam of X-rays after passage at least partially through an object in said gantry intermediate said scan target and said detector means, and for providing data proportional thereto for use in computer reconstruction of an image of a portion of said object, said detector means being concentric with and defining a plane normal to said axis of symmetry;

wherein said electron beam is produced along a beam source axis that is offset relative to said axis of symmetry.

2. The system of claim 1, wherein said beam source axis is offset in position and angle relative to said axis of symmetry.

3. The system of claim 1, wherein said beam source axis is parallel to said axis of symmetry but is not co-axial therewith.

4. The system of claim 1, wherein said drift tube is straight.

5. The system of claim 1, wherein said drift tube is kinked.

6. The system of claim 1, further including means, disposed intermediate said first and second regions, for controlling ions in chosen regions of said chamber.

7. The system of claim 1, further including means for maintaining at least one desired characteristic of said beam spot along said scan target.

8. The system of claim 7, wherein said means for maintaining includes a tuning target having a plurality of "W"-shape electron beam intercepting devices therein, said devices producing electrical signals upon electron beam impingement, which signals vary as a characteristic of said electron beam.

9. The system of claim 1, further including couch means for moving a patient through said gantry for X-ray examination, said couch means having a location selected from the group consisting of (i) an "upstream" location, and (ii) a "downstream" location.

* * * * *